US005783733A

United States Patent [19]
Kissinger

[11] Patent Number: 5,783,733
[45] Date of Patent: Jul. 21, 1998

[54] PROCESS FOR MANUFACTURE OF BISPHENOL

[75] Inventor: Gaylord Michael Kissinger, Evansville, Ind.

[73] Assignee: General Electric Company, Pittsfield, Mass.

[21] Appl. No.: 664,079

[22] Filed: Jun. 13, 1996

[51] Int. Cl.$^6$ .......................... C07C 39/12; C07C 39/16
[52] U.S. Cl. ........................ 568/724; 568/727; 568/728
[58] Field of Search ................................ 568/722, 724, 568/727, 728

[56] References Cited

U.S. PATENT DOCUMENTS

| | | |
|---|---|---|
| 3,326,986 | 6/1967 | Dugan . |
| 4,294,995 | 10/1981 | Faler . |
| 4,346,247 | 8/1982 | Faler . |
| 4,365,099 | 12/1982 | Faler et al. . |
| 4,375,567 | 3/1983 | Faler . |
| 4,396,728 | 8/1983 | Faler . |
| 4,584,416 | 4/1986 | Pressman . |
| 4,590,303 | 5/1986 | Mendiratta . |
| 4,847,433 | 7/1989 | Kissinger . |
| 4,876,391 | 10/1989 | Kissinger . |
| 4,876,395 | 10/1989 | Kissinger . |
| 5,075,511 | 12/1991 | Li . |
| 5,105,027 | 4/1992 | Desmurs et al. . |
| 5,146,007 | 9/1992 | Cipullo . |
| 5,210,329 | 5/1993 | Gomes de Matos et al. . |
| 5,243,093 | 9/1993 | Kissinger et al. . |
| 5,315,042 | 5/1994 | Cipullo . |
| 5,362,900 | 11/1994 | Kissinger . |
| 5,399,789 | 3/1995 | Cipullo et al. . |
| 5,414,152 | 5/1995 | Cipullo . |
| 5,434,316 | 7/1995 | Kissinger . |
| 5,475,152 | 12/1995 | Kissinger et al. . |

*Primary Examiner*—Gary Geist
*Assistant Examiner*—Karl J. Puttlitz, Jr.

[57] ABSTRACT

An integrated process for the preparation and recovery of a bisphenol based on the condensation reaction of a ketone and a phenol in the presence of an ion-exchange resin.

17 Claims, 1 Drawing Sheet

PROCESS FOR MANUFACTURE OF BISPHENOL

BACKGROUND OF THE INVENTION

The invention relates to a process for the manufacture of bisphenol.

Dihydric phenols have achieved significant success in many commercial applications. Dihydric phenols are useful in the commercial manufacture of various polymers including polyarylates, polyamides, epoxies, polyetherimides, polysulfones and polycarbonates. Significant attention has been directed to the commercial manufacture of dihydric phenols. For example, it is well known that the acid catalyzed reaction of phenol with specific aldehydes or ketones would prepare the 4,4'-dihydric phenol. In particular when phenol is reacted with acetone, the dihydric phenol 2,2-bis (4-hydroxy-phenyl)propane, also known as bisphenol-A or BPA is formed, which has particular utility in the manufacture of polycarbonates, polyarylates and copolyestercarbonates as well as epoxies. In order to make such polymers, in particular polycarbonates, the bisphenol-A must be particularly pure, for example, as measured by color. Additionally, the process should be particularly efficient with respect to selectivity, yield and energy use, since the dihydric phenol is a substantial portion of the final polymer.

The art is replete with references directed to the preparation of bisphenol-A. For many years, one of the particularly useful catalysts described in the patent art and employed commercially has been hydrochloric acid (HCl). In such a previously known method, glass lined vessels are charged in a batch/continuous fashion, with phenol, acetone and recycled by-products from earlier synthesis. This mixture is continually kept under a positive pressure of HCl gas, which catalyzes the formation of BPA and its by-products. The acetone is reacted to essentially complete depletion. The effluent from said phenol/acetone reaction is sent to an acid removal unit. In this unit HCl, water and some phenol are removed along with only a trace amount of unreacted acetone. Once HCl has been removed, the remainder of the stream, containing the water of condensation, BPA and unreacted phenol and acetone, is sent to a phenol stripping unit where phenol and acetone are removed by distillation. In the process of the present invention the HCl removal step is eliminated so that the effluent from the phenol/acetone reaction unit is sent directly to the phenol stripping unit. BPA effluent from the distillation unit is then sent to another unit to be purified by a fractional melt crystallization process. The method involves purifying impure BPA by fractional melt crystallization in a falling film dynamic crystallizer. Purified BPA is recovered from the melt crystallizer as flakes by solidifying the molten BPA on a cooled rotating drum. Recycle residue from the melt crystallizers, containing BPA, phenol, tar, and isomers, is sent to a recovery unit to separate the phenol and bisphenol-A from the tar and isomers. The BPA is then returned to the melt crystallizer feed while the phenol, tar and isomers are sent to the tar/isomer cracker. The tar/isomer cracker is a combination reactor/distillation column that uses a cracking catalyst, such as sodium hydroxide or sulfonic acids, to break down the isomers and other impurities. The phenol recovered from the tar/isomer cracker is returned to the reaction and the residue or tar from this cracker is either sold or burned for fuel value.

The following results were obtained using the described prior art HCl process with recycle impurities.

TABLE 1

| | Reaction Feed | | Reaction Effluent | |
|---|---|---|---|---|
| Component | Range | Component | Range |
| $H_2O$ | 0.2%–0.4% | $H_2O$ | 0.2%–3.0% |
| Acetone | 7.0%–8.0% | Acetone | 0.0%–0.2% |
| Phenol | 81.0%–8.0% | Phenol | 58.0%–65.0% |
| p,p'-BPA | 3.0%–8.0% | p,p'-BPA | 28.0%–34.0% |
| o,p'-BPA | 0.5%–1.0% | o,p'-BPA | 1.0%–1.5% |
| Dimer | 0.2%–0.3% | Dimer | 0.25%–0.35% |
| BPX I | 0.2%–0.3% | BPX I | 0.25%–0.3% |
| Chroman | 0.2%–0.4% | Chroman | 0.35%–0.5% |
| Spiro | 0 | Spiro | 0 |
| BPX II | 0.1%–0.2% | BPX II | 0.1%–0.2% |
| Unknowns | 0.04%–0.5% | Unknowns | 0.7%–0.9% |
| HCl | gas blanket | HCl | 1.0%–3.0% |

Although the above process has high conversion of the reactants to BPA, acid resistant equipment is required. Hydrochloric acid is highly corrosive and ordinary metallic reactors and piping must be changed on a frequent basis. Glass lined vessels and other exotic equipment is often used; however, the use of such equipment requires great care because it is easily damaged. Also, losses of the acid are high which requires acid replacement for continued effective operation. In addition, caustic is required to neutralize the acid which results in substantial waste discharge of salts. Another disadvantage is that equipment is needed to regenerate HCl and to remove water.

A method of making BPA using an ion exchange resin (IER) catalyst is described in U.S. Pat. No. 4,375,567, incorporated herein by reference. The method as described in '567 consists of transporting effluent to a BPA concentrator, a crystallizer and a solid/liquid separator to effect the separation of BPA from its reaction by-product and starting reactants which are recycled to an isomerization zone containing an ion-exchange catalyst to effect the conversion of said 2,4'-dihydroxy-2,2-diphenyl propane to 2,2-bis(4-hydroxyphenyl)propane which is recycled to a bisphenol feed tank. Although this method eliminates the need for acid resistant equipment, it requires the use of a multitude of purification process equipment.

The present invention is based on the discovery of a fully integrated bisphenol process, which results in high purity bisphenol. Additionally, the process of the present invention is simpler than any integrated process presently known. It uses less energy, reduces organic emissions, reduces operating complexity, as well as lowers maintenance requirements.

SUMMARY OF THE INVENTION

In accordance with the invention, there is provided a process for making a bisphenol which comprises:

(a) reacting a phenol with a ketone in the presence of an ion exchange resin catalyst to produce bisphenol;

(b) separating unreacted phenol from the bisphenol produced in step (a) in a phenol removal unit;

(c) extracting water and acetone from said separated phenol in a mother liquor dryer unit to obtain a dried phenol and returning the dried phenol to said reactor;

(d) separating the extracted water from the extracted acetone of step (c) in a waste water purification unit and returning said acetone to said reactor and transferring said water to a water discharge facility;

(e) separating phenol, isomers, and tar from said bisphenol obtained from the phenol removal unit in a melt crystallizer by fractional melt crystallization in a falling film dynamic crystallizer;

(f) transferring recycle residue which comprises bisphenol, phenol, tars, and isomers from said melt crystallizer to a recycle recovery unit;

(g) recovering bisphenol from the recycle recovery unit and returning recovered bisphenol to the melt crystallizer;

(h) transferring residual phenol, tars and isomers from said recycle recovery unit to a tar/isomer recovery unit;

(i) recovering phenol from the tar/isomer cracker wherein the phenol is returned to the reactor and the tar is disposed of; and (j) recovering in a bisphenol recovery unit purified bisphenol from the melt crystallizer.

BRIEF DESCRIPTION OF DRAWING

The accompanying drawing is a block diagram showing an embodiment of the inventive process.

DESCRIPTION OF THE INVENTION

Figure 1:
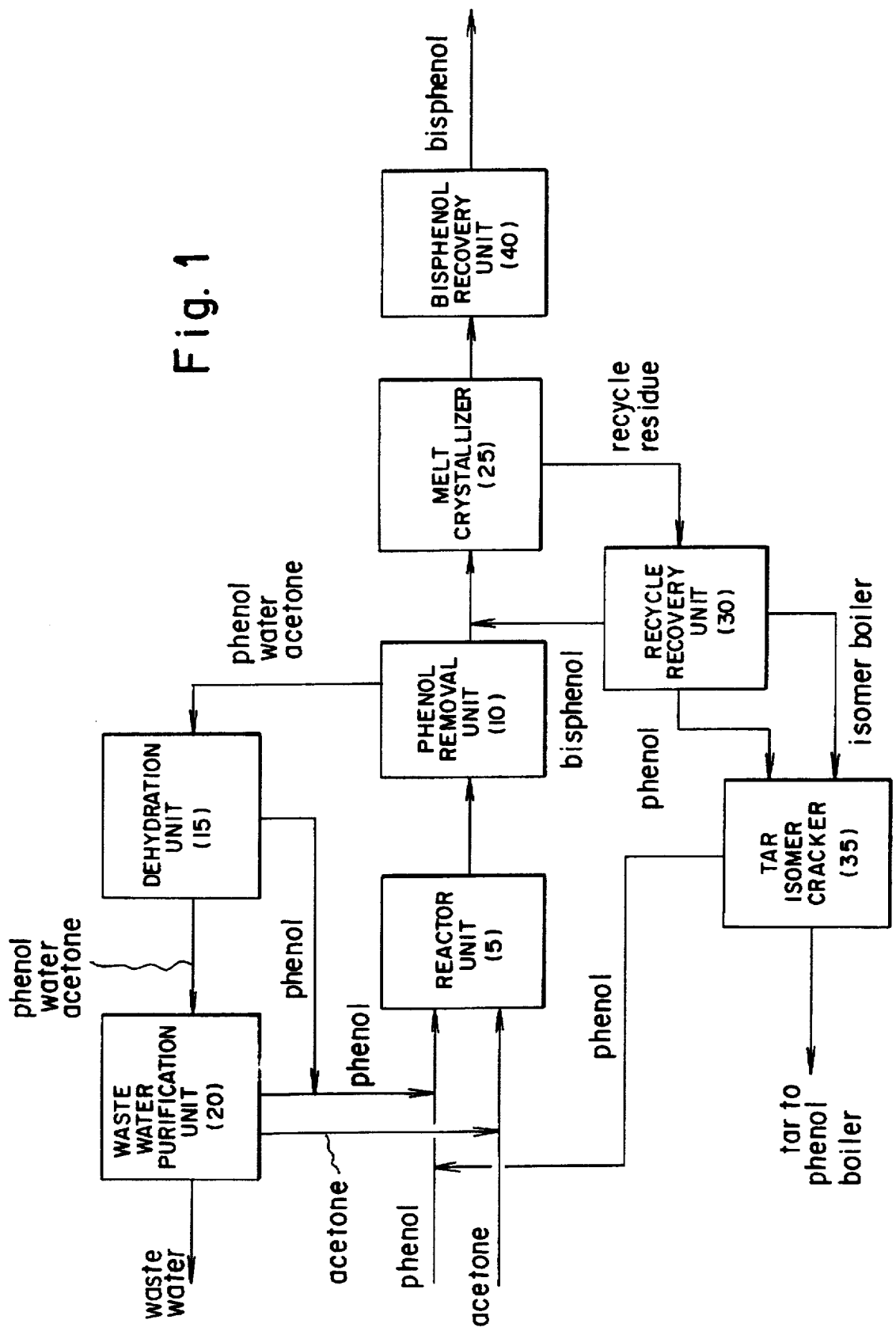

In order that those skilled in the art will be better able to practice the invention, reference is made to the drawing. There is shown in the schematic a reactor (5) in which phenol, usually in excess, is reacted with a ketone in the presence of an ion exchange resin (IER) catalyst to produce crude bisphenol. Such reactor can be a batch reactor, continuous reactor or other reactor used by those skilled in the art to effect reactions of this type. Reactor (5) is joined to a phenol removal unit (10) in which phenol is separated from the bisphenol leaving a crude bisphenol containing less than about 1% phenol. The crude bisphenol from the phenol removal unit (10) is fed to a melt crystallizer (25), while the removed phenol and unreacted acetone/water stream is fed to a dehydration unit (15). Waste water from the dehydration unit (15), containing small amounts of phenol, acetone and by-products, is then sent to a waste water purification unit (20). Phenol from the dehydration unit (15) bottom is recycled back to the reactor (5). Recovered phenol and acetone from the waste water purification unit (20) is then recycled to the reactor (5). The purified bisphenol from the melt crystallizer (25) is sent to bisphenol recovery (40), whereas the recycle residue from the melt crystallizer (25), containing bisphenol, phenol, tar and isomers, is sent to a recycle recovery unit (30). The bisphenol recovered in the recycle recovery unit (30) is returned to the melt crystallizer (25) and the remaining products from the recycle recovery unit (30), the phenol, tar and isomers, flow to a tar/isomer cracker (35). The recovered phenol from the tar/isomer cracker (35) is returned to the reactor (5), and the tar is burned or sold for fuel value.

The reaction consists of passing phenol and acetone through a stationary bed of IER catalyst. This reaction can be done in one of two ways: first, until essentially complete acetone depletion or secondly, and preferably, by using a partial acetone conversion (PAC) method. The PAC method, described in U.S. Pat. No. 5,315,042, incorporated herein by reference, comprises the steps of contacting phenol and acetone in the presence of an acidic catalyst under accelerated flow conditions or increased throughput such that the initial production of BPA is increased. The acetone and BPA are separated from the effluent stream prior to depletion of the acetone whereby the residence time of the BPA is reduced and undesirable by-products and color are reduced. The IER reactor effluent, which contains no "free acid", but only unreacted acetone, phenol, bisphenol-A and its by-products, along with a promoter such as 3-mercaptopropionic acid, or ethyl, methyl or propyl mercaptan, is fed to a removal system which removes the water of reaction, residual acetone, and phenol. Reaction is initiated by heating the phenol and acetone under substantially anhydrous conditions, that is less than 2% by weight of water and preferably less than 0.2% by water content weight, to reaction temperature. The reactants are passed through a fixed porous bed of ion-exchange resin at a slight pressure to maintain adequate flow, although gravity pressure is also found to be satisfactory.

Phenol removal in phenol removal unit (10) can be done via nitrogen desorption or through distillation. It is preferred that the crude bisphenol composition contain no more than 10 weight percent phenol. More preferably less than about 7 weight percent of the crude bisphenol composition is phenol. Still more preferably the crude bisphenol composition contains less than about 1% phenol.

The crude bisphenol from the phenol removal unit (10) is fed to the melt crystallizer (25) for purification. The method involves purifying the crude bisphenol by fractional melt crystallization, in a falling film dynamic crystallizer, for example, as described in U.S. Pat. No. 5,475,152, incorporated herein by reference. In a multiple stage fractional melt crystallizer, the crystalline component's purity is upgraded in each successive stage, through the phases of crystallization, partial melting (sweating), and total melting. A preferred apparatus to carry out the fractional melt crystallization is manufactured by Sulzer Canada, Inc., a subsidiary of Sulzer Brothers, Ltd., Switzerland. In this manner, highly pure bisphenol can be obtained without contamination by extraneous solvents or other materials. Along with para, para bisphenol, said crude bisphenol composition may contain side reaction products such as ortho, para bisphenol, chroman, BPXs, dimers, spirobiindane and isopropenylphenol. The said melt crystallization operation results in a purified bisphenol product of better than about 99.5%, preferably better than 99.8% and most preferably better than 99.9% purity.

The by-products from the melt crystallization unit (25), containing bisphenol, phenol, tar and isomers, are sent to a recycle recovery unit (30). The bisphenol recovered in the recycle recovery unit (30) is returned to the melt crystallizer feed, and the phenol, tar, and isomers flow to the tar/isomer cracker (35).

The tar/isomer cracker (35) is a combination reactor/distillation column which uses a caustic such as sodium hydroxide to break down the tar, isomers, and other residue. Residue is distilled at a temperature of about 270° F. to remove a light fraction and an intermediate fraction between about 372° F. and about 390° F. under a pressure of about 4 mm Hg. The tar/isomer cracker (35) operates advantageously at a temperature of from about 310° F. to about 510° F. under atmospheric pressure. The phenol recovered from the tar/isomer cracker (35) is returned to the reactor (5) and the residue or tar from this cracker is either sold or burned for fuel value.

The molten, purified bisphenol from the melt crystallizer (25) is recovered in a bisphenol recovery unit (40). The said bisphenol can be recovered as "flakes" by solidifying the melt on a cold rotating drum or as "prills" from a prilling operation. Both methods are well known in the chemical industry for recovering molten products.

The unreacted phenol from the phenol removal unit (10) of the process is sent to a dryer to extract the water and acetone from the said removed phenol at a temperature of from about 126° F. to about 202° F. This is the unreacted acetone and water of reaction from the partial acetone conversion reaction along with some phenol, which is part of the azeotrope. The major portion of the phenol, with the acetone and water/phenol azeotrope removed, is recycled back the reactor (5).

The water and unreacted acetone along with traces of phenol are then sent to a waste water purification unit (20), wherein said unreacted acetone and phenol is returned to the reactor (5) and the water is transferred to a waste water discharge facility. The preferred process uses solvents such as toluene or methylisobutylketone in a counter current liquid/liquid extraction column to remove the acetone and phenol from the water of reaction. The water is processed through a stripper to remove the solvent before discharge to the waste water treatment plant to remove the solvent. The phenol and acetone are distilled from the solvent, separated and returned to reaction.

The process can be practiced with a bulk promoter catalyst or an attached promoter catalyst, with and without recycle impurities.

The process employing a bulk promoter catalyst with recycle impurities is described as follows:

The reactor employed is capable of utilizing either full or partial acetone conversion technology with a weighted hourly space velocity (WHSV) between 0.2–5.0. The reactor feed stream consists of 74–84 percent by weight phenol, between 3.0–8.0 percent by weight acetone, and a mercaptan promoter, with the balance consisting of recycle bisphenol-A and recycle impurities. The reactor effluent temperature is typically between 175° F.–200° F. Phenol stripping is accomplished using vacuum distillation or inert gas desorption. A typical distillation column will have a bottom temperature of between 275° F.–325° F., and at a below atmospheric pressure of between 100–175 mmHg. Desorption is accomplished by passing an inert gas, such as nitrogen, counter-current to the product feed in a packed column, with phenol being condensed and separated from the gas flow stream. A typical desorber will have a bottom and inert gas temperature between 325° F.–385° F. The composition of the material from the distillation/desorption fed to the crystallizers is about as follows: 70–85 percent by weight p,p'-bisphenol-A, and 15–30 percent by weight reaction by-products. Residue from this step is sent to recovery where bisphenol-A is recovered and then returned to the melt crystallizer feed. Light and heavy fractions from recycle recovery are partially recycled and partly purged to a catalytic cracker, yielding phenol. The recovered phenol is recycled back to reaction. The composition of the final product should be about 99.9+percent by weight p,p'-bisphenol-A, and about 0.1 percent by weight other.

The following results were obtained using the PAC reaction process as disclosed above.

TABLE 2

| Reaction Feed | | Reaction Effluent | |
|---|---|---|---|
| Component | Range | Component | Range |
| H₂O | 0.04%–0.15% | H₂O | 0.95%–1.5% |
| Acetone | 3%–8% | Acetone | 0.5%–1.5% |
| Phenol | 74%–84% | Phenol | 58%–65% |
| p,p'-BPA | 8%–15% | p,p'-BPA | 24%–32% |
| o,p'-BPA | 2.7%–3.4% | o,p'-BPA | 3%–4% |
| Dimer | 0.4%–0.55% | Dimer | 0.5%–0.8% |

TABLE 2-continued

| Reaction Feed | | Reaction Effluent | |
|---|---|---|---|
| Component | Range | Component | Range |
| BPX I | 1%–1.4% | BPX I | 1.3%–1.8% |
| Chroman | 0.7%–1.1 | Chroman | 0.85%–1.2% |
| Spiro | 0 | Spiro | 0 |
| BPX II | 0.3%–0.5% | BPX II | 0.3%–0.5% |
| Unknowns | 0.0%–0.03% | Unknowns | 0.0%–0.03% |

The following results were obtained using the full acetone conversion reaction process as disclosed above with recycle impurities.

TABLE 3

| Reaction Feed | | Reaction Effluent | |
|---|---|---|---|
| Component | Range | Component | Range |
| H₂O | 0.025%–0.35% | H₂O | 1.3%–1.8% |
| Acetone | 3%–8.% | Acetone | 0.1%–0.3% |
| Phenol | 74%–84% | Phenol | 62%–68% |
| p,p'-BPA | 8%–15% | p,p'-BPA | 21%–27% |
| o,p'-BPA | 2%–3% | o,p'-BPA | 2.0%–3.2% |
| Dimer | 3%–4% | Dimer | 3.0%–4.2% |
| BPX I | 0.5%–1.% | BPX I | 0.5%–1.5% |
| Chroman | 0.5%–1% | Chroman | 0.5%–1.5% |
| Spiro | 0.1%–0.4% | Spiro | 0.1%–0.7% |
| BPX II | 0.25%–0.75% | BPX II | 0.3%–0.9% |
| Unknowns | 0.0%–0.1% | Unknowns | 0.0%–0.2% |

The process employing PAC and an attached promoter catalyst with and without recycle impurities is described as follows:

The IER reactor is capable of using between 2–35 mole percent of the sulfonic acid groups neutralized with mercaptoethyl amine. This system utilizes partial acetone conversion technology with a WHSV between 0.2–20.0. The reactor feed stream consists of pure phenol, between 3.0–8.0 percent by weight acetone, and recycle impurities. The reactor effluent temperature is typically between 150° F.–200° F. Phenol stripping can be accomplished using vacuum distillation or inert gas desorption. A typical distillation column will have a bottom temperature of between 275° F.–325° F., and at below atmospheric pressure of between 100–175 mmHg. Desorption is accomplished by passing an inert gas, such as nitrogen, counter-current to the product feed in a packed column, with phenol being condensed and separated from the gas flow stream. A typical desorber will have a bottom and inert gas temperature between 325° F.–385° F. The composition of the material from the distillation/desorption fed to the crystallizers is about as follows: 80–96 percent by weight p,p'-bisphenol-A, and 4–20 percent by weight reaction by-products. Residue from this step is sent to recycle recovery where bisphenol-A is recovered and then returned to the melt crystallizer feed. Light and heavy fractions from recycle recovery are partially recycled and partly purged to a catalytic cracker, yielding phenol. The recovered phenol is recycled back to reaction. The composition of the final product should be about 99.9+percent by weight p,p'-bisphenol-A, and about 0.1 percent by weight other.

The following results were obtained using the process as disclosed above without recycle impurities.

TABLE 4

| Reaction Feed | | Reaction Effluent | |
| --- | --- | --- | --- |
| Component | Range | Component | Range |
| H₂O | 0 | H₂O | 0.5%–1% |
| Acetone | 3%–8% | Acetone | 0.1%–3% |
| Phenol | 92%–97% | Phenol | 83%–87% |
| p,p'-BPA | 0 | p,p'-BPA | 11%–30% |
| o,p'-BPA | 0 | o,p'-BPA | 0.3%–0.8% |
| Dimer | 0 | Dimer | 0.03%–0.07% |
| BPX I | 0 | BPX I | 0.1%–0.7% |
| Chroman | 0 | Chroman | 0 |
| Spiro | 0 | Spiro | 0.0%–0.03% |
| BPX II | 0 | BPX II | 0.0%–0.06% |
| Unknowns | 0 | Unknowns | 0.04%–0.1% |

The following results were obtained using the process as disclosed above with recycle impurities.

TABLE 5

| Reaction Feed | | Reaction Effluent | |
| --- | --- | --- | --- |
| Component | Range | Component | Range |
| H₂O | 0.25%–0.35% | H₂O | 0.75%–1.2% |
| Acetone | 3%–8% | Acetone | 0.5%–3% |
| Phenol | 74%–84% | Phenol | 67%–71% |
| p,p'-BPA | 8%–15% | p,p'-BPA | 17%–30% |
| o,p'-BPA | 2%–3% | o,p'-BPA | 2%–3% |
| Dimer | 3%–4% | Dimer | 3%–4% |
| BPX I | 0.5%–1% | BPX I | 0.9%–1.1% |
| Chroman | 0.5%–1% | Chroman | 0.5%–0.7% |
| Spiro | 0.1%–0.4% | Spiro | 0.08%–0.12% |
| BPX II | 0.25%–0.75% | BPX II | 1%–1.3% |
| Unknowns | 0.0%–0.1% | Unknowns | 0.9%–1.1% |

As shown in the tables above, the IER reaction provides quite different results than the HCl reaction. However, the end product of the integrated process is identical to the end product of the prior art process. The following end product results were achieved using the processes as disclosed above.

TABLE 6

| Prior Art Process HCl Crystallizer Effluent | | Invention Process IER Crystallizer Effluent | |
| --- | --- | --- | --- |
| Componen | Average | Componen | Average |
| p,p'-BPA | 99.9040% | p,p'-BPA | 99.9091% |
| o,p'-BPA | 0.0610% | o,p'-BPA | 0.0350% |
| Dimer | 0.0120% | Dimer | 0.0081% |
| BPX I | 0.0030% | BPX I | 0.0061% |
| Chroman | 0.0040% | Chroman | 0.0003% |
| Spiro | 0.0000% | Spiro | 0.0000% |
| BPX II | 0.0010% | BPX II | 0.0114% |
| Unknowns | 0.0150% | Unknowns | 0.0300% |

It was unexpected that the said IER reaction process produced such high purity bisphenol while using less energy and simplifying the integrated bisphenol reaction process without the harmful chemicals used in the HCl process. Chlorine emissions, of six pounds 33% HCl per hundred pounds BPA, were eliminated. In addition, the equipment employed in the process of the present invention lasts indefinitely whereas the HCl process equipment life is limited. It has been shown that the instant invention surprisingly provides a more efficient, dependable, and environmentally safe process for manufacturing bisphenols than any previously known bisphenol processes.

What is claimed is:

1. A process for making bisphenols which comprises:
   (a) reacting a phenol with a ketone in the presence of an ion exchange resin catalyst to produce bisphenol;
   (b) separating unreacted phenol from the bisphenol produced in step (a) in a phenol removal unit;
   (c) extracting water and acetone from said separated phenol in a dehydration unit to obtain a dried phenol and returning the dried phenol to said reactor;
   (d) separating the extracted water from the extracted acetone of step (c) in a waste water purification unit and returning said acetone to said reactor and transferring said water to a water discharge facility;
   (e) separating phenol, isomers, and tar from said bisphenol obtained from the phenol removal unit in a melt crystallizer by fractional melt crystallization in a falling film dynamic crystallizer;
   (f) transferring recycle residue which comprises bisphenol, phenol, tars, and isomers from said melt crystallizer to a recycle recovery unit;
   (g) recovering bisphenol from the recycle recovery unit and returning recovered bisphenol to the melt crystallizer;
   (h) transferring residual phenol, tars and isomers from said recycle recovery unit to a tar/isomer recovery unit;
   (i) recovering phenol from the tar/isomer cracker wherein the phenol is returned to the reactor and the tar is disposed of; and
   (j) recovering in a bisphenol recovery unit purified bisphenol from the melt crystallizer.

2. A method in accordance with claim 1 wherein the purity of the purified bisphenol is better than about 99.8%.

3. A method in accordance with claim 2 wherein the purity of the purified bisphenol is better than about 99.9%.

4. The method in accordance with claim 1, wherein the bisphenol is bisphenol-A.

5. The method in accordance with claim 1, wherein the reaction is an excess of a phenol with a ketone.

6. The method in accordance with claim 1, wherein reaction of the phenol with the ketone in step (a) utilizes partial acetone conversion.

7. The method in accordance with claim 1, wherein reaction is a continuous process.

8. The method in accordance with claim 1, wherein reaction occurs in a batch reactor.

9. The process of claim 1 wherein the distillation performed in step (b) is carried out at a temperature of about 410° F. and under a reduced atmospheric pressure of about 35 mm Hg absolute.

10. The process of claim 1 wherein step (c) is carried out by liquid-liquid extraction at a temperature from about 126° F. to about 202° F.

11. The process of claim 1 wherein the reaction of phenol and ketone in step (a) is carried out at a temperature from about 175° F. to about 200° F.

12. The process of claim 1 wherein the recycle residue from the melt crystallizer is distilled at a temperature of about 273° F. to remove a light fraction and an intermediate fraction between about 372° F. and about 390° F. under a pressure of about 4 mm Hg.

13. The process of claim 1 wherein recovery of phenol from step (i) is carried out by catalytic cracking is carried out at a temperature from about 310° F. to about 510° F.

14. The process of claim 1 wherein the purified bisphenol from the melt crystallizer is flaked in a bisphenol recovery unit.

15. The process of claim 1 wherein the purified bisphenol from the melt crystallizer is prilled in a bisphenol recovery unit.

16. The product made in accordance with claim 1.

17. A process for making bisphenols consisting essentially of:

(a) reacting a phenol with a ketone in the presence of an ion exchange resin catalyst to produce bisphenol;

(b) separating unreacted phenol from the bisphenol produced in step (a) in a phenol removal unit;

(c) extracting water and acetone from said separated phenol in a mother liquor dryer unit to obtain a dried phenol and returning the dried phenol to said reactor;

(d) separating the extracted water from the extracted acetone of step (c) in a waste water purification unit and returning said acetone to said reactor and transferring said water to a water discharge facility;

(e) separating phenol, isomers, and tar from said bisphenol obtained from the phenol removal unit in a melt crystallizer by fractional melt crystallization in a falling film dynamic crystallizer;

(f) transferring recycle residue which comprises bisphenol, phenol, tars, and isomers from said melt crystallizer to a recycle recovery unit;

(g) recovering bisphenol from the recycle recovery unit and returning recovered bisphenol to the melt crystallizer;

(h) transferring residual phenol, tars and isomers from said recycle recovery unit to a tar/isomer recovery unit;

(i) recovering phenol from the tar/isomer cracker wherein the phenol is returned to the reactor and the tar is disposed of; and (j) recovering in a bisphenol recovery unit purified bisphenol from the melt crystallizer.

* * * * *